(12) United States Patent
Leuthardt et al.

(10) Patent No.: US 8,761,869 B2
(45) Date of Patent: Jun. 24, 2014

(54) BRAIN FUNCTION MAPPING

(75) Inventors: Eric Claude Leuthardt, St. Louis, MO (US); Jonathan Dean Breshears, St. Louis, MO (US)

(73) Assignee: Washington University, St. Louis, MO (US)

( * ) Notice: Subject to any disclaimer, the term of this patent is extended or adjusted under 35 U.S.C. 154(b) by 181 days.

(21) Appl. No.: 13/149,356

(22) Filed: May 31, 2011

(65) Prior Publication Data

US 2011/0295143 A1 Dec. 1, 2011

Related U.S. Application Data

(60) Provisional application No. 61/349,969, filed on May 31, 2010.

(51) Int. Cl.
*A61B 5/04* (2006.01)

(52) U.S. Cl.
USPC .......................................................... 600/544

(58) Field of Classification Search
USPC .................................................. 600/544, 545
See application file for complete search history.

(56) References Cited

U.S. PATENT DOCUMENTS 6,167,298 A * 12/2000 Levin ............................ 600/545
2004/0092809 A1 * 5/2004 DeCharms .................... 600/410

OTHER PUBLICATIONS

Biyu J. He, et al., Electrophysicological Correlates of the Brain's Intrinsic Large-Scale Functional Architecture, PNAS, pp. 16039-16044, vol. 105, No. 41, 2008, Neuroscience.

Nitish Kumar, Brain Computer Interface, A Seminar Report, Jun. 2009, 52 pages, http://www.seminarprojects.com/Thread-brain-computer-interface-a-seminar-report.

Biyu J. He and Marcus E. Raichle, The fMRI Signal, Slow Cortical Potential and Consciousness, 2009, p. 302-309, Cell Press, Opinions, 2009, Elsevier.

Jess Bartels et al., Neurotrophic Electrode: Method of Assembly and Implantation into Human Motor Speech Cortex, pp. 168-176, J. Neurosci Methods, vol. 174(2), 2008, NIH Public Access Author Manuscript.

Electrocorticography, Wikipedia Contributors, Feb. 2010, p. 1-6, http://en.wikipedia.org/wiki/Electrocorticography.

Zhang X., et al., Social network theory applied to resting-state fMRI connectivity data in the identification of epilepsy networks with iterative feature selection, pp. 129-139, Journal of Neuroscience Methods, vol. 199, 2011, ScienceDirect, Elsevier.

Woodward, Neil D., et al, Functional Resting-State Networks are Differentially Affected in Schizophrenia, pp. 86-93, Schizophrenia Research, vol. 130, 2011, Elsevier.

Lui S., et al., Resting-State Functional Connectivity in Treatment-Resistant Depression, 13 pages, AJP in Advance, 2011, American Psychiatric Association.

(Continued)

*Primary Examiner* — Navin Natnithithadha
*Assistant Examiner* — Etsub Berhanu
(74) *Attorney, Agent, or Firm* — Armstrong Teasdale LLP

(57) ABSTRACT

A method for identifying a functional area of a brain. The functional area is associated with a neurological function. The method includes applying a plurality of electrodes to a surface of the brain. A slow cortical potential is determined based on one or more electrical signals produced by the plurality of electrodes. A covariance pattern is computed based on the slow cortical potential, and the configuration of co-varying electrodes is used to identify one or more areas of the brain associated with the neurological function. These co-varying patterns may be used in conjunction with other electrical and/or physiological stimulation paradigms.

20 Claims, 16 Drawing Sheets

(56) References Cited

OTHER PUBLICATIONS

Carter A. R. et al., Resting Interhemispheric Functional Magnetic Resonance Imaging Connectivity Predicts Performance After Stroke, pp. 365-376, 2010, American Neurological Association.

Chen G., et al., Classification of Alzheimer Disease, Mild Cognitive Impairment, and Normal Cognitive Status with Large-Scale Network Analysis Based on Resting-State Functional MR Imaging, pp. 213-221, Radiology, vol. 259 (1), 2011.

Assaf M. et al., Abnormal Functional Connectivity of Default Mode Sub-Networks in Autism Spectrum Disorder Patients, pp. 247-256, Neuroimage, vol. 53(1), 2010, NIH Public Access, Author Manuscript.

Bush G., Attention-Deficit/Hyperactivity Disorder and Attention Networks, pp. 278-300, Neurophsychopharmacology Review, vol. 35(1), 2010, npg.

Breshears, Jonathan D., The Dynamic and Stable Cortical Electrophysiology of Conscious State Transitions with Propofol Asnesthesia and its Implications for Mapping Functional Cortex in Unconscious Patients, pp. 1-27, 2010, MA/MD Thesis.

Mircea Steriade, et al., Dyanamic Properties of Corticothalamic Neurons and Local Cortical Interneurons Generating Fast Rhythmic (30-40 Hz) Spike Bursts, pp. 483-490, Rapid Communication, 1998, The American Physiological Society.

Aura Silva, et al., Comparison of Anesthetic Depth Indexes Based on Thalamocortical Local Field Potentials in Rats, pp. 355-363, Anesthesiology, vol. 112, 2010, The American Society of Anesthesiologists, Inc., Lippincott Williams & Wilkins.

Nicholas D. Schiff and Fred Plum, The Role of Arousal and "Gating" Systems in the Neurology of Impaired Consciousness, pp. 438-452, Journal of Clinical Neurophysiology, vol. 17(5), 2000, American Clinical Neurophysiology Society.

Gerwin Schalk, et al., BCI2000: A General-Purpose Brain-Computer Interface (BCI) System, pp. 1034-1043, IEEE Transactions on Biomedical Engineering, vol. 51, No. 6, 2004, IEEE.

Ramachandran Ramani, MD, et al., Sevoflurane 0.25 MAC Preferentially Affects Higher Order Association Areas: A Functional Magnetic Resonance Imaging Study in Volunteers, pp. 648-655, Anesthesia & Analgesia, vol. 105, No. 3, 2007, International Anesthesia Research Society.

Kai J. Miller, et al., Cortical Electrode Localization from X-Rays and Simple Mapping for Electrocorticographic Research: The "Location on Cortex" (LOC) Package for MATLAB, pp. 303-308, Journal of Neuroscience Methods, vol. 162, 2007, Elsevier B.V.

R. Llinas, et al., The Neuronal Basis for Consciousness, pp. 1841-1849, Philosophical Transactions of The Royal Society Biological Sciences, vol. 353, 1998, http:///rstb.royalscoietypublishing.org.

R. Llinas and U. Ribary, Coherent 40-Hz Oscillation Characterizes Dream State in Humans, pp. 2078-2081, Proc. Natl. Acad. Sci., vol. 90, 1993, Neurobiology.

Eric C. Leuthardt, et al., A Brain-Computer Interface Using Electrocorticographic Signals in Humans, p. 63-71, Journal of Neural Engineering, vol. 1, 2004, Institute of Physics Publishing.

Uncheol Lee, et al., Propofol Induction Reduces the Capacity for Neural Information Integration: Implications for the Mechanism of Consciousness and General Anesthesia, pp. 56-64, Consciousness and Cognition, vol. 18, 2009, Elsevier.

Ruut M. Laitio, MD, et al., Effects of Xenon Anesthesia on Cerebral Blood Flow in Humans, A Positron Emission Tomography Study, pp. 1128-1133, Anesthesiology, vol. 106, No. 6, 2007, The American Society of Anesthesiologists, Inc. Lippincott Williams & Wilkins, Inc.

K. Kuizenga, et al., Biphasic EEG Changes in Relation to Loss of Consciousness During Induction with Thiopental, Propofol, Etomidate, Midazolam or Sevoflurane, pp. 354-360, British Journal of Anaesthesia, vol. 86, No. 3, 2001, The Board of Management and Trustees of the British Journal of Anaesthesia.

Matthew D. Krasowski, et al., Propofol and Other Intravenous Anesthetics have Sites of Action on the y-Aminobutyric Acid type A Receptor Distinct from That for Isoflurane, pp. 530-538, Molecular Pharmacology, vol. 53, 1998, The American society for Pharmacology and Experimental Therapeutics.

Max B. Kelz, et al., An Essential Role for Orexins in Emergence from General Anesthesia, pp. 1309-1314, PNAS, vol. 105, No. 4, 2008, The National Academy of Sciences of the USA.

Kaike K. Kaisti, MD., et al., Effects of Sevoflurance, Propofol, and Adjunct Nitrous Oxide on Regional Cerebral Blood Flow, Oxygen Consumption, and Blood Volume in Humans, pp. 603-613, Anesthesiology, vol. 99, 2003, American Society of Anesthesiologists, Inc. Kippincott Williams & Wilkins, Inc.

Michael S. Jones, et al., Intracellular Correlates of Fast (>200Hz) Electrical Oscillations in Rat Somatosensory Cortex, 1505-1518, J. Neurophysiol, vol. 84, 2000.

Edward G. Jones, Thalamic Circuitry and Thalamocortical Synchrony, pp. 1659-1673, Philosophical Transactions of The Royal Society B, vol. 357, 2002, Biological Sciences, http://rstb.royalsocietypublishing.org/content/357/1428/1659#related-urls.

M. Joliot, et al., Human Oscillatory Brain Activity Near 40 Hz Coexists with Cognitive Temporal Binding, pp. 11748-11751, Proc. Natl. Acad. Sci, USA, vol. 91, 1994, Neurobiology.

E.R. John, et al., Invariant Reversible QEEG Effects of Anesthetics, pp. 165-183, Consciousness and Cognition, vol. 10, 2001, Academic Press.

William Sukov and Daniel S. Barth, Three-Dimensional Analysis of Spontaneous and Thalamically Evoked Gamma Oscillations in Auditory Cortex, pp. 2875-2884, J. Neurophysiol, vol. 79, 1998, The American Physiological Society.

Walter J. Freeman, et al., Spatial Spectra of Scalp EEG and EMG from Awake Humans, pp. 1053-1068, Clincial Neurophysiology, vol. 114, 2003, Elsevier.

Nicholas P. Franks, General Anaesthesia: From Molecular Targets to Neuronal Pathways of Sleep and Arousal, p. 370-386, www.nature.com/reviews.neuro, vol. 9, 2008, Nature Publishing Group.

Pierre Fiset, et al., Brain Mechanisms of Propofol-Induced Loss of Consciousness in Humans: a Positron Emission Tomographic Study, The Journal of Neuroscience, pp. 5506-5513, vol. 19, No. 13, 1999, Society of Neuroscience.

Erik Edwards, et al., High Gamma Activity in Response to Deviant Auditory Stimuli Recorded Directly From Human Cortex, J. Neurophysiol, pp. 4269-4280, vol. 94, 2005.

N.E. Crone, et al., Electrocorticographic Gamma Activity During Word Production in Spoken and Sign Language, Neurology, pp. 2045-2053, vol. 57, 2001, American Academy of Neurology.

Mary Ann Cheng, MD, et al., Large-Dose Propofol Alone in Adult Epileptic Patients: Electrocorticographic Results, pp. 169-174, Anesthesia & Analgesia, vol. 83, 1996, International Anesthesia Research Society.

R. T. Canolty, et al., High Gamma Power is Phase-Locked to Theta Oscillations in Human Neocortex, pp. 1626-1628, Science, vol. 313, 2006, AAAS.

M. T. Alkire, et al., Toward a Unified Theory of Narcosis: Brain Imaging Evidence for a Thalamocortical Switch as the Neurophysiologic Basis of Anesthetic-Induced Unconsciousness, pp. 370-386, Consciousness and Cognition, vol. 9, 2000, Academic Press.

Nathan S. White and Michael T. Alkire, Impaired Thalamocortical Connectivity in Humans During General-Anesthetic-Induced Unconsciousness, pp. 402-411, NeuroImage, vol. 19, 2003, Academic Press.

J. L. Vincent, et al., Intrinsic Functional Architecture in the Anaesthetized Monkey Brain, pp. 83-88, Nature Letters, vol. 447, 2007, Nature Publishing Group.

Sunao Uchida, et al., Suppression of Gamma Activity in the Human Medial Temporal Lobe by Sevoflurane Anesthesia, pp. 39-42, Neurophysiology, Basic and Clinical, NeuroReport, vol. 11, No. 1, 2000, Lippincott Williams & Wilkins.

* cited by examiner

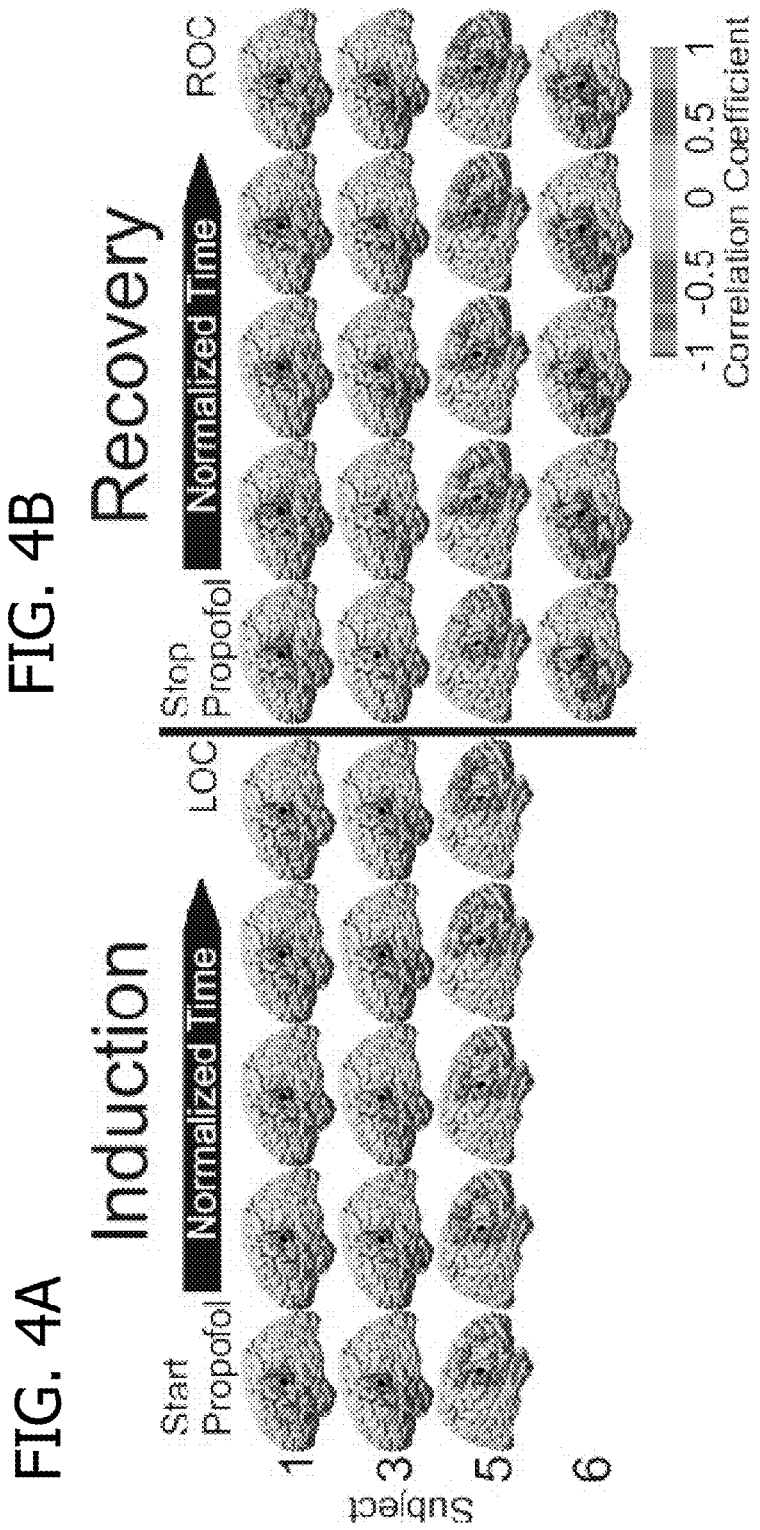

Subject 2

Subject 5

Subject 6

BRAIN FUNCTION MAPPING

CROSS REFERENCE TO RELATED APPLICATIONS

This application claims the benefit of Provisional Patent Application Ser. No. 61/349,969 entitled "BRAIN FUNCTION MAPPING", which was filed on May 31, 2010 and which is hereby incorporated by reference in its entirety.

BACKGROUND

Precise localization of eloquent cortex is a clinical necessity prior to surgical resections adjacent to speech or motor cortex. In the intraoperative setting, this traditionally requires that a portion of the surgery have the patient awake and inducing temporary lesions by direct electrocortical stimulation (DECS). This portion of the case can be stressful for the patient and requires they be conscious and cooperative. In the extraoperative setting, where grid electrodes are placed on the surface of the brain, mapping is time consuming, cumbersome, and also requires the patient's active participation. In both scenarios the use of DECS also has elevated risks of inducing seizures that can further complicate the patients mapping and can be dangerous to the patient. In an attempt to increase efficiency and potentially reduce the amount of necessary stimulation, using the intrinsic physiology of the brain to define important functional networks could give comparable amounts of information in localizing important neurologic functions without the need for the patient to be awake during a surgery, participate in a cognitive paradigm, or even be conscious. This also may reduce or eliminate the need for cortical stimulation.

Every year millions of people undergo general anesthesia, yet the mechanism(s) by which widely used clinical anesthetics are able to reversibly ablate consciousness remains incompletely understood. Thus far, the majority of studies in humans have utilized non-invasive methods such as functional imaging and electroencephalography (EEG) to arrive at the current understanding. Both modalities show there is a complex interplay between and within the thalamus and the cortex. Numerous positron emission tomography (PET) studies have demonstrated that the thalamus is a common site of deactivation during induction by various anesthetic agents. Further, disruption of thalamo-cortical and cortico-cortical connectivity assessed by PET was found to be correlated with the loss of consciousness. The consistency of thalamic involvement across different anesthetic agents supports its role as a possible "off-switch" during anesthetic induced unconsciousness. Additionally, PET and functional magnetic resonance imaging (fMRI) studies have demonstrated that specific regions of association cortices show enhanced deactivation with certain anesthetics. Because of the low temporal resolution of these imaging modalities, however, the interplay of thalamic and cortical physiologies is difficult to define.

BRIEF DESCRIPTION

In one aspect, a method for identifying a functional area of a brain is provided. The functional area is associated with a neurological function. The method includes applying a plurality of electrodes to a surface of the brain. A slow cortical potential is determined based on one or more electrical signals produced by the plurality of electrodes. A covariance pattern is computed based on the slow cortical potential. One or more areas of the brain associated with the neurological function are identified based on the covariance pattern.

In another aspect, a method for identifying a functional area of a brain is provided. The functional area is associated with a neurological function. The method includes applying a plurality of electrodes to a surface of the brain. A slow cortical potential is determined based on one or more electrical signals produced by the plurality of electrodes. A covariance pattern is computed based on the slow cortical potential to identify one or more areas associated with the neurological function. A sensory stimulus associated with the neurological function is applied to elicit a physiologic response. A plurality of activated electrodes within the plurality of electrodes is identified. The activated electrodes demonstrate a physiological response to the stimulus. The activated electrodes are used as seeds to identify one or more other electrodes that covary with the activated electrodes.

BRIEF DESCRIPTION OF THE DRAWINGS

FIG. 4A is an illustration of the correlation coefficient ($p<0.001$) of the slow cortical potential ($<0.1$ Hz) with an inferior motor cortex seed electrode in four patients with preferential somatomotor coverage during induction.

FIG. 4B is an illustration of the correlation coefficient ($p<0.001$) of the slow cortical potential ($<0.1$ Hz) with an inferior motor cortex seed electrode in four patients with preferential somatomotor coverage during recovery.

DETAILED DESCRIPTION

Figure 1:
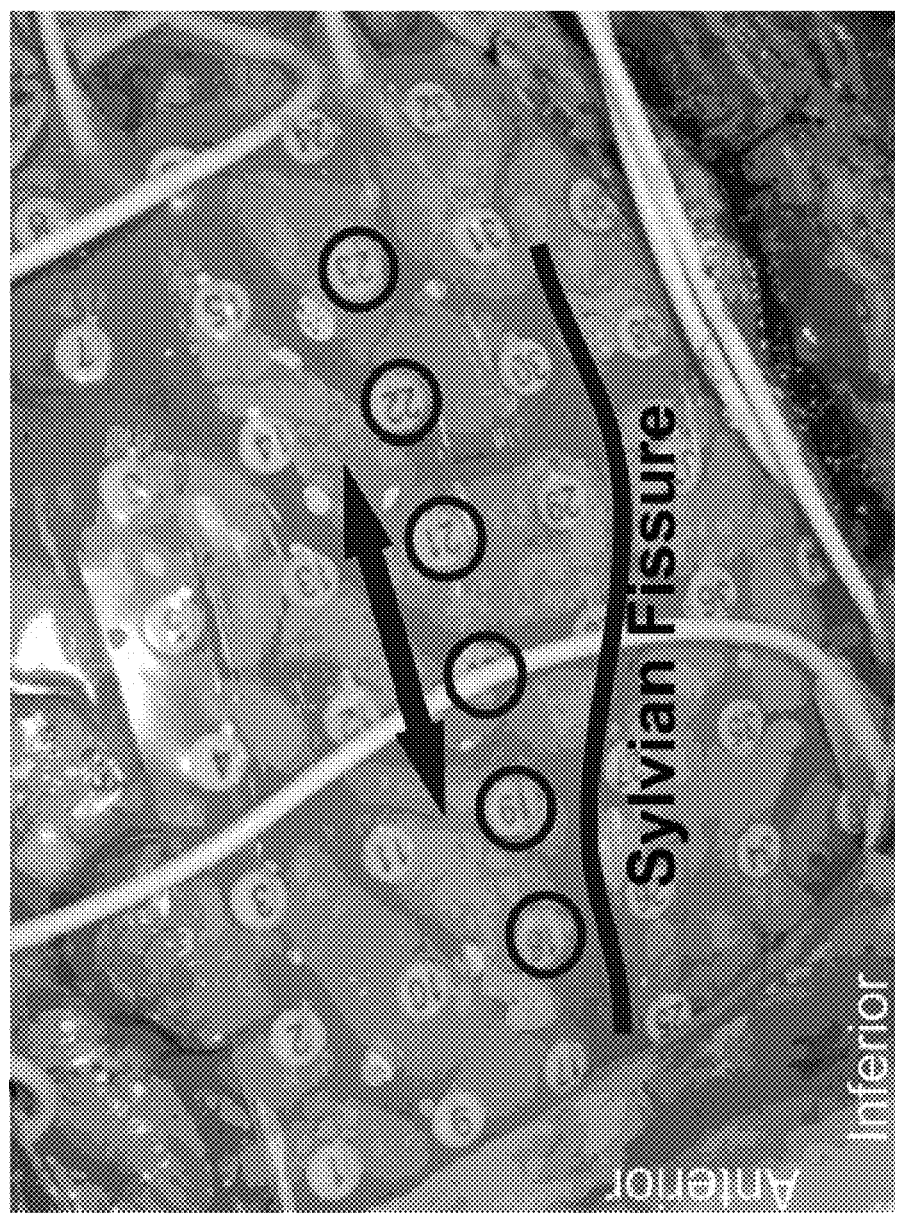
FIG. 1 is an illustration of a method of systematic seed selection.

Embodiments described herein facilitate identifying one or more functional areas of a brain. In one embodiment, such identification is provided via a method by which, after recording electrical potentials directly from the exposed cortex of an anesthetized or otherwise unresponsive neurosurgical patient, the cortical areas responsible for speech and motor, and other networked functions in that individual are identified intraoperatively by analysis of the covariance patterns of the slow cortical potential (<0.5 Hz) which are stable and present regardless of the depth of anesthesia or degree of unresponsiveness.

Electrodes showing a consistent covariance pattern may be referred to as a network. The configuration of such networks may be used to determine the neurological function of one or more regions of the brain. The one or more areas of the brain associated with the neurological function that can be identified can be associated with one or more of the following: speech; motor function; vision; attention; and hearing. The one or more areas of the brain associated with the neurological function can include identifying one or more areas of the brain associated with neurodegenerative disorders. In addition, these networks may be used with established stimulation and mapping paradigms and/or methods to identify seed regions of interest. Covariance patterns networked with a site of interest are identified. An anatomic distribution of a plurality of covariance patterns can further be compared to other anatomic data. The anatomic distribution of a plurality of covariance patterns compared to other anatomic data can include comparing the anatomic distribution to magnetic resonance imaging data. The anatomic distribution of a plurality of covariance patterns compared to other anatomic data can include comparing the anatomic distribution to functional magnetic resonance imaging data. The anatomic distribution of a plurality of covariance patterns compared to other anatomic data can include comparing the anatomic distribution to computed tomography data. The anatomic distribution of a plurality of covariance patterns compared to other anatomic data can include comparing the anatomic distribution to positron emission tomography data. The anatomic distribution of a plurality of covariance patterns compared to other anatomic data can include comparing the anatomic distribution to imaging data representing resting state functional connectivity.

Such neurological functions may be part of normal human cognitive operations that may be stimulated to elicit a physiological response. Stimuli associated with such neurological functions include, without limitation, auditory stimuli, painful and/or proprioceptive stimuli, visual stimuli, olfactory stimuli, taste stimuli, and motor stimuli. Moreover, such neurological functions may be part of abnormal human cognitive operations, including, without limitation, epileptic seizures, schizophrenia, autism, mood disorders (e.g., depression), attentional disorders (e.g., attention deficit disorder), and strokes.

In one embodiment, by using gamma frequency (>50 Hz) activations in auditory cortex evoked in response to hearing spoken language (known to occur in unconscious subjects), it is possible to identify electrodes over auditory cortex which can then be used as seeds for computing the covariance structure of the slow cortical potential (SCP). Since the SCP is an electrical correlate of the fMRI BOLD signal, these covariance patterns reveal the brain's intrinsic functional networks, and a seed over auditory cortex will reveal a networked relationship with both Wernicke's and Broca's speech areas. Additionally, motor cortex can be intraoperatively defined with SCP covariance patterns. There is currently no method of identifying speech cortex in unresponsive and/or anesthetized individuals.

Rapid timescales of anesthesia's effect on brain activity have been assessed using electroencephalography or EEG. Electrical potentials acquired from the scalp provide millisecond resolution of broad cortical changes. EEG based studies also support the dual role that cortex and thalamus play in anesthesia-altered consciousness. It has been observed that there was an increase in power of low frequencies (<25 Hz) and a decrease in power of high frequencies (25-50 Hz) which was consistent across multiple anesthetic agents and reversible upon recovery. This shift in power towards lower frequencies was thought to result from a hyperpolarization of the thalamus that results in a change in firing of thalamocortical neurons from a tonic to a bursting pattern. The higher frequencies, or gamma rhythms, are thought to result from small ensembles of cortical neurons firing in synchrony and are associated with higher cognitive operations. Thus, their decline with anesthesia has been posited to represent a suppression of cortex and a reduced ability to integrate information. The full scope of the cortical activity revealed with EEG, however, is limited due to the poor anatomic resolution, limited frequency bandwidth, and poor signal-to-noise ratio of the signal.

To date, many studies have focused primarily on the induction of anesthesia, while recovery has been less thoroughly studied. Recent evidence suggests that recovery may not simply be the inverse of induction, but rather the two processes demonstrate a hysteresis effect. In the context of consciousness this is of central importance. These findings imply that the neural mechanisms that govern the loss and recovery of consciousness may be distinct. To address some of the limitations of non-invasive approaches and to better define the effect of anesthesia on human cortex with both the loss and recovery of consciousness, we capitalize on the unique clinical scenario of invasive electrocorticographic (ECoG) monitoring of patients during induction and recovery from propofol anesthesia. By recording electrical activity directly from the surface of the cortex, ECoG provides a powerful method to integrate the spatial, temporal, and spectral features of human cortical physiology not possible with other non-invasive modalities.

In this study, we report the first comprehensive recording of invasive ECoG activity from human subjects during both induction and recovery from propofol anesthesia. These recordings allow a more granular analysis of the electrophysiologic behavior of cortex during loss and recovery of consciousness, which we define in this context as the ability to follow verbal commands, or responsiveness. During these transitions there are distinct cortical dynamics that are represented by changes in power, variance, and covariance that occur at different frequency bands. Delta-high gamma power alterations and mu-beta-low gamma variance/covariance demonstrated independent timescales with evolving depth of anesthesia, which then reversed somewhat asymmetrically on recovery. There were also cortical interactions characterized by the slow cortical potentials and theta-gamma power oscillations that remained stable throughout the induction and recovery process. These findings demonstrate that anesthesia-induced alterations of consciousness are characterized by dynamic changes in cortex that are ordered in time and characterized by different frequency spectra. In addition to these changing dynamics, there are also stable cortical interactions that do not change and support a concomitant functional architecture that is maintained throughout the loss and recovery of consciousness.

These maintained functional networks have strong anatomic correspondence to networks defined by fMRI BOLD (Blood Oxygen Level Dependent) signal covariance. Therefore, an important clinical implication of these maintained electrical networks is the ability to identify functional cortex in unconscious surgical patients from baseline data, a feat not before possible. Initial assessments indicate that methods described herein facilitate identifying the somatomotor cortex in unresponsive surgical patients.

Subjects

Eight patients undergoing surgical treatment for intractable epilepsy participated in this study, which was approved by the Human Research and Protection Organization at Washington University School of Medicine. Prior to inclusion, all patients gave written informed consent. Exclusion criteria included the presence of dysplastic cortex on clinical magnetic resonance imaging. Each patient underwent craniotomy for the subdural placement of an electrode array which was then removed (with a second craniotomy) one week later for resection of the epileptic foci. Electrophysiological data was acquired from these patients under two scenarios: 1) during the recovery from anesthesia after the initial craniotomy, and 2) during the induction of anesthesia prior to the second craniotomy. See Table S1 below for demographic and clinical information.

Equipment

ECoG signals were recorded and digitized from the implanted electrode array at a sampling rate of 1200 Hz using g.tech (Graz, Austria) biosignal amplifiers. The data was stored by a Dell PC running BCI2000 which time-locked the acquired ECoG signal. The ECoG electrode array (AdTech, Racine, Wis., USA) contained 48 to 64 platinum electrodes which had 2.3 mm diameter exposed surface and were spaced 10 mm apart.

Data Collection

After closure of the surgical wound, the implanted electrode array was connected to the amplifiers and additional cortical or skull electrodes provided the reference and ground. Skull electrodes consisted of an intracranial electrode strip (1×4) that faced the inner table of the skull. A cortical reference was used to avoid the high impedance of a standard skull reference electrode making poor contact due to an immediate post-surgically diminished brain volume. Signal acquisition began when the propofol infusion, used for anesthetic maintenance during the craniotomy, was stopped. Signal acquisition continued until the return of consciousness (ROC) had been established. ROC was defined as the point when the patient was able to follow a verbal command, such as "squeeze my hand." One week later, prior to surgery to remove the electrodes and resect the epileptic foci, data was collected during the induction of propofol anesthesia. The electrode array was connected to the amplifiers, and cortical or skull electrodes provided the ground and reference. Data acquisition began with the start of propofol infusion (Medfusion 2010, Duluth, Ga., USA) and continued until the completion of tracheal intubation. The loss of consciousness (LOC) was noted as the point prior to intubation when the patient no longer followed verbal commands as described above. Propofol was infused in a continuous and controlled fashion, incrementally titrating up the dose to achieve a prolonged pharmacologic transition from a pre-induction state of responsiveness to a final state of unresponsiveness. Due to propofol's highly variable effects amongst individuals, this titration was based on clinical observation of spontaneous eye opening, movements and reaction to environmental stimuli. The Bispectral Index (BIS) score was manually recorded approximately every 30 seconds during both the induction and recovery data collection.

Artifact Removal from ECoG Data

Signals from every electrode were visually inspected and those identified as having predominately poor signal-to-noise characteristics were excluded from further analysis. Segments of artifact in the remaining signals were manually removed. Remaining signals were re-referenced to the common mean. Artifact removal resulted in discarding signals from 83 of 720 recorded ECoG electrodes, and manual artifact removal resulted in discarding 9% of the remaining ECoG signal.

Spectral Power Analysis

Although other signals may be collected, only recovery signals acquired between the discontinuation of propofol and the ROC, and induction signals acquired between the start of propofol infusion and the LOC, were included in the following analysis unless explicitly stated otherwise. Spectral analysis was done by signal convolution with a Gabor wavelet library. The time-varying power was computed for frequencies ranging from 0.1 to 205 Hz. A frequency resolution of 1 Hz bins was used below 10 Hz, while 2 Hz bins were used from 11 Hz to 45 Hz. Above 75 Hz, bins of 5 and 10 Hz were used. Known noise bands at 60, 120, 180, 215, and 240 Hz were intentionally avoided by skipping a 30 Hz wide band centered on each peak (a 20 Hz band was avoided around the 215 Hz noise peak). Analysis of trends in the time-varying absolute band power, and variance in band power followed. The spectral power was grouped into nine frequency bands: $\delta$ (1-2 Hz), $\theta$ (3-8 Hz), $\mu$ (9-11 Hz), $\beta_1$ (13-21 Hz), $\beta_2$ (23-35 Hz), $\gamma_1$ (37-45 Hz), $\gamma_2$ (75-105 Hz), $\gamma_3$ (135-165 Hz), and $\gamma_4$ (195-205 Hz). Absolute band power changes at each electrode were determined using the MATLAB robust fit algorithm to fit the slope.

To cortically localize these power changes at each electrode, the getLOC package for MATLAB was used to get the Tailarach coordinates of the electrodes from the lateral skull radiographs. Global time-varying trends of the absolute band power were found by smoothing the spectral data from each electrode with a 1 second moving average and down-sampling to one sample per second. For each subject, trends were combined across electrodes by taking the median. These absolute band power trends were then normalized by the maximum. Temporal normalization between the standardized endpoints was also done by dividing by the time to LOC or ROC for induction and recovery, respectively. The data was then linearly interpolated to equate the number of sample points between subjects; this allowed for combining data across subjects.

The variance in relative power was computed for each frequency band using a 30 second sliding window. Intra-band covariance trends were analyzed by computing the covariance of the band limited power between all combinations of electrode pairs using a 30 second sliding window. The median of this time-varying covariance was found across all electrode pairs. Finally, absolute band power, variance, and covariance in band power data was combined across 7 patients for induction and 6 patients for recovery by finding the median value and bootstrapping a 95% confidence interval at each sample point.

Slow Cortical Potential Covariance

To investigate the behavior of the somatomotor network, covariance of the slow cortical potential (>0.1 Hz), shown to be related to fMRI BOLD signal, was computed in a subset of subjects with preferential motor coverage. Covariance was computed in five consecutive windows for both induction and recovery, using an electrode selected over inferior motor cortex as the seed. Further, to determine the behavior of these covariance patterns at extreme depths of anesthesia, data recorded during periods of burst suppression from 3 subjects was analyzed in using the same seed.

Phase-Power Analysis

The relationship between the phase of lower frequencies ranging from 0 to 25 Hz and the power in all nine frequency bands was examined. The raw ECoG signal was bandpass-filtered with a zero-phase shift, and the signal was divided into four consecutive epochs. Within each epoch, the band power and filtered signal were aligned to the troughs of the filtered signal with 500 ms lead and lag times, and averaged. The covariance was then computed between the trough-aligned average of the filtered signal and power for the nine frequency bands. The resulting statistically significant ($P<0.001$) correlation coefficients were averaged across electrodes for individual patients, then combined across patients by averaging.

To investigate with finer resolution the temporal progression of the phase-power relationship between specific frequencies, the same analysis was performed using 50 consecutive time epochs. The results were combined across patients by taking the median and bootstrapping a 95% confidence interval for each epoch. Finally, the trends in power, variance, covariance, and phase-power coupling were modeled using adaptive piecewise linear regression to identify knots that improved the coefficient of determination ($R^2$) over a simple linear model. Segments of the model were constrained to be linear and a generalized cross-validation penalty per knot of 10 was used.

Correspondence of SCP Correlation During Unconsciousness to Electrocortical Stimulation (ECS) Mapping To assess how well SCP covariance networks in unresponsive/unconscious subjects corresponded to functional cortex defined by ECS mapping, the distribution of pair-wise correlation scores for intra-versus extra-network electrodes were compared. These SCP correlations were computed on the first two minutes of data collected during recovery prior to the subject reaching responsiveness. For subjects without recovery data, the last two minutes of induction, after the LOC, were used.

Sensitivity and Specificity of SCP Covariance for Identifying Somatomotor Cortex To investigate the potential of SCP covariance networks as a tool for the operative mapping of somatomotor cortex in anesthetized patients, the sensitivity and specificity of three approaches to identifying functional somatomotor cortex was assessed. The first approach was based on eigenvalue decomposition of the covariance matrix of the SCP at each electrode, or principal component analysis. Using the ECS results as the gold standard for comparison, the sensitivity and specificity of the top 15 principal components was calculated for 7 subjects individually and cumulatively. The second approach to using SCP covariance for mapping was affinity propagation clustering of the electrodes based on their SCP covariance patterns. The sensitivity and specificity of the 10 largest clusters was calculated for 7 subjects individually and cumulatively. Finally, the sensitivity and specificity of systematic seed selection was calculated. This method involved systematically using electrodes superior to the visually identified Sylvian fissure as seeds and sequentially progressing in a path parallel to the fissure (FIG. 1). Due to the bipolar stimulation of ECS mapping, a true positive was defined as identifying at least one of the two stimulated electrodes which caused a motor or sensory response.

FIG. 1 is an illustration of a method of systematic seed selection. SCP covariance pattern is analyzed for seed electrodes running in a path parallel and superior to the visually identified Sylvian fissure.

Figure 2A:
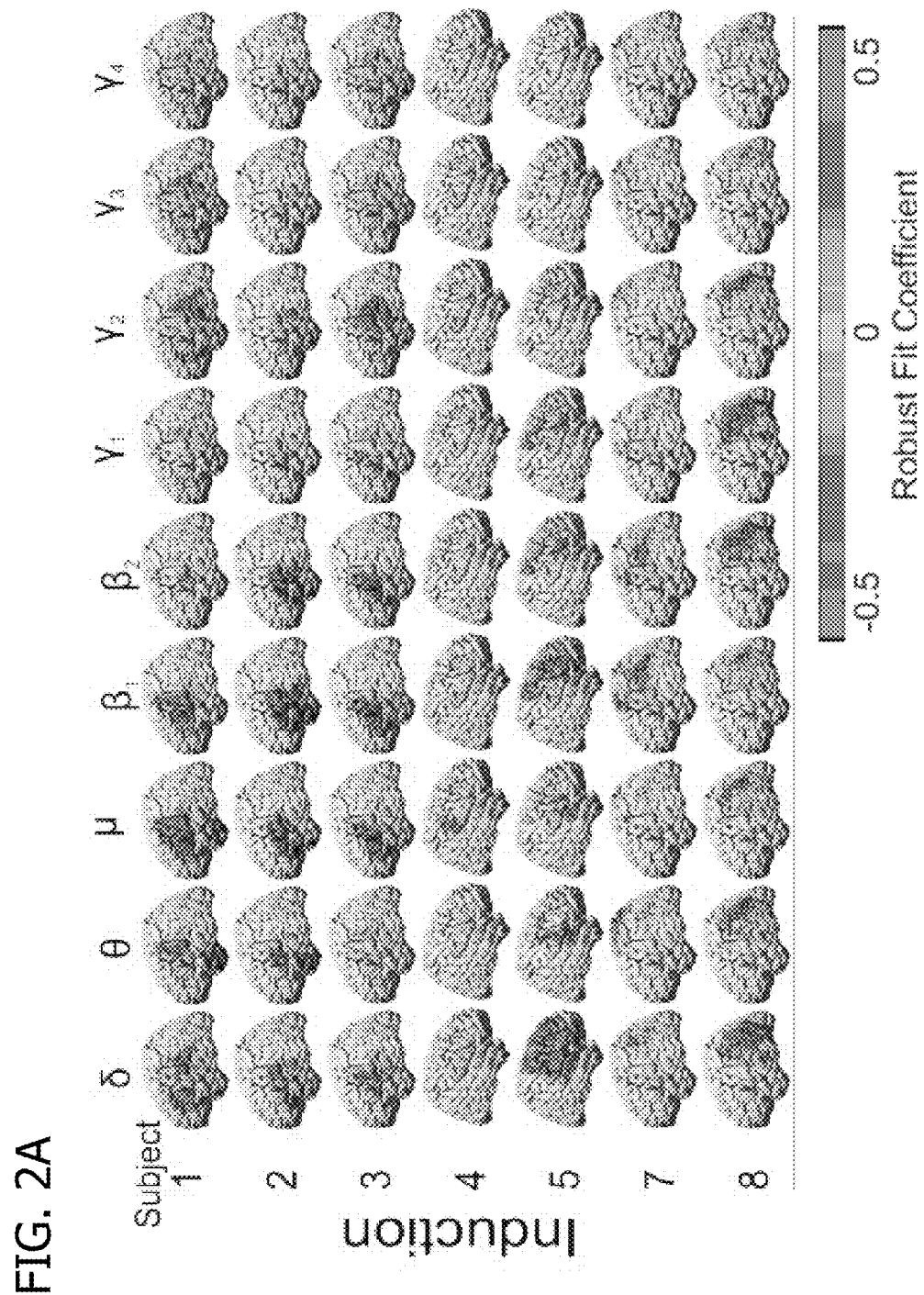
FIG. 2A is an illustration of topographic absolute power changes during induction.
Figure 2B:
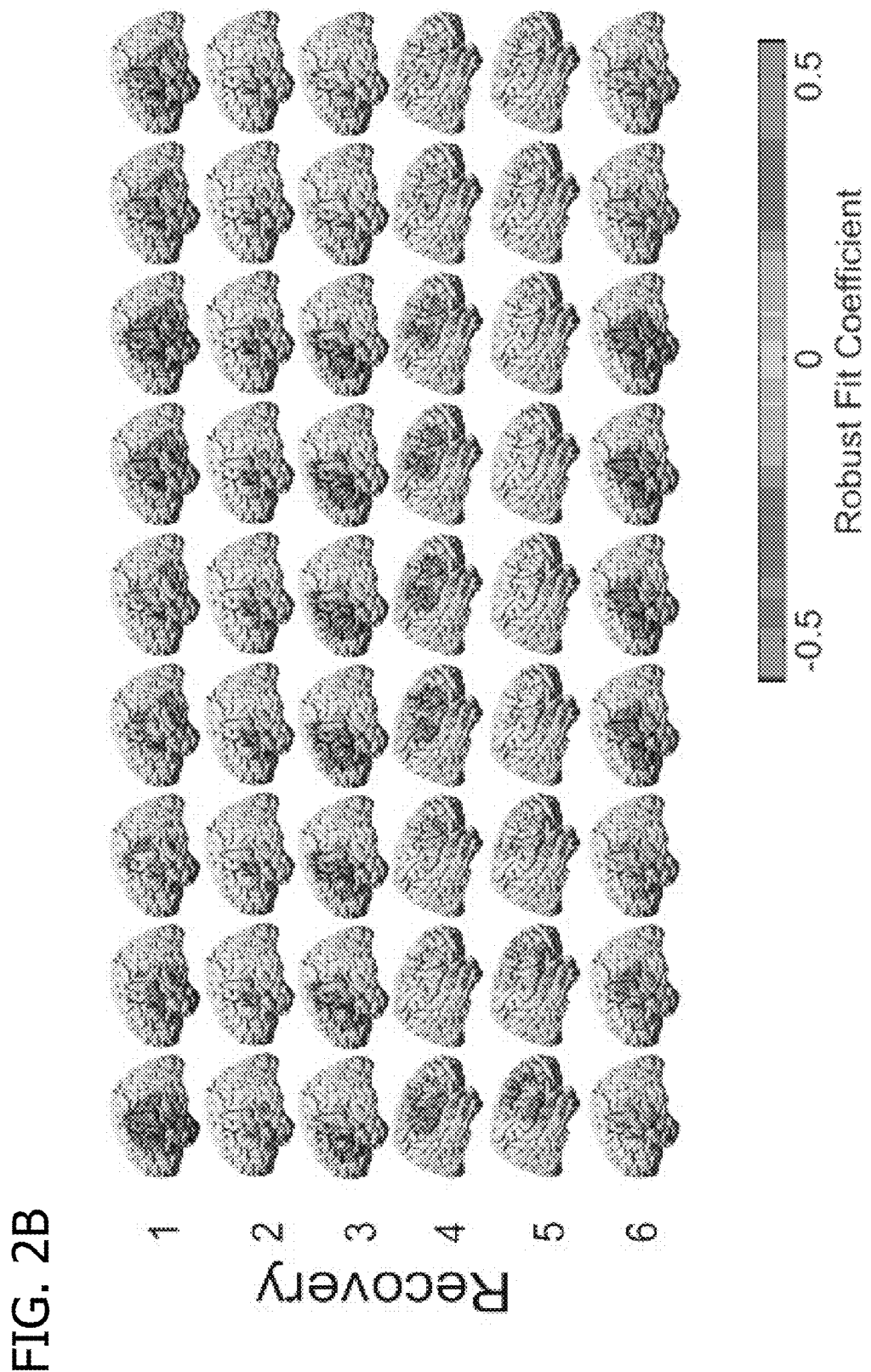
FIG. 2B is an illustration of topographic absolute power changes during recovery.

The absolute band power changes at each electrode are displayed topographically by frequency band in FIGS. 2A and 2B. The robust fit coefficients ($p<0.001$), indicated by color, reflect the absolute power increases or decreases at the corresponding electrode location.

FIG. 2A is an illustration of topographic absolute power changes during induction. FIG. 2B is an illustration of topographic absolute power changes during recovery. The robust fit coefficients ($p<0.001$) of the absolute band power at each electrode during induction (FIG. 2A) and recovery (FIG. 2B) is shown for the nine frequency bands. As shown in FIG. 2A, during induction, the $\gamma_{1-4}$ band power primarily decreased, with the most consistent decreases occurring in the $\gamma_2$ band. Power in the $\theta$-$\beta_2$ bands demonstrated anatomically heterogeneous and variable changes. The $\delta$ band power predominately increased during induction. As shown in FIG. 2B, during recovery, the $\delta$, $\theta$, and $\mu$ band power primarily decreased, while power in the $\beta_1$-$\gamma_4$ bands showed increases The $\delta$ band demonstrated an increase on induction and a decrease on recovery, while $\gamma_{1-4}$ bands were found to have the opposite trends. The $\gamma_{2-4}$ bands showed little inter-subject or anatomic variability and the changes were statistically significant across subjects as indicated by the 95% confidence intervals (n=7 for induction, n=6 for recovery). The $\theta$, $\mu$, and $\beta_{1-2}$ bands displayed greater inter-subject and anatomic variability, with $\theta$ and $\mu$ showing no significant trends across subjects. $\beta_{1-2}$ showed ambiguous behavior during induction, but showed a significant increase in power during recovery.

Figure 3A:
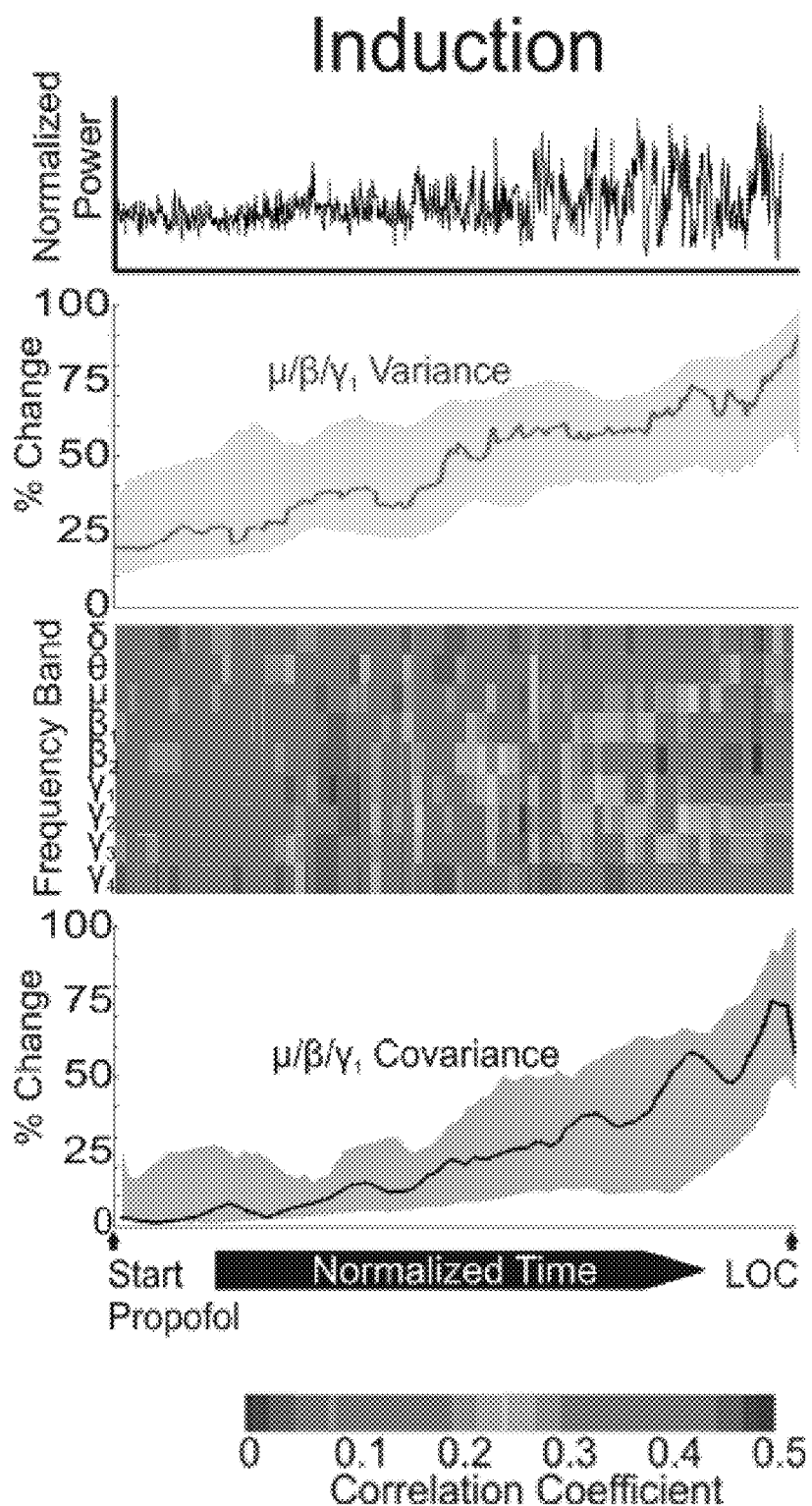
FIG. 3A is an illustration of trends in $\mu$, $\beta$, and $\gamma_1$ power variability and covariance between distant cortical sites during induction.
Figure 3B:
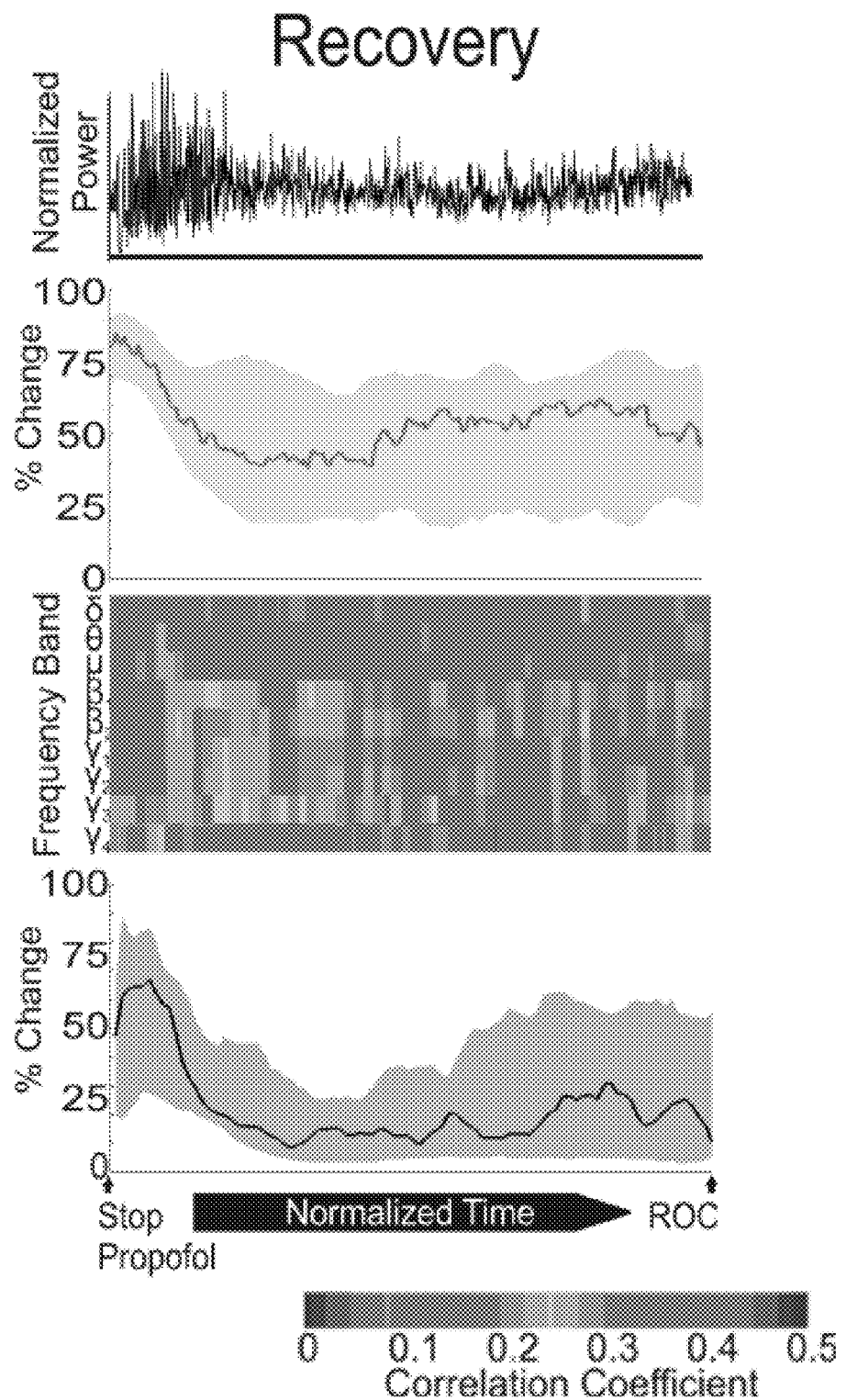
FIG. 3B is an illustration of trends in $\mu$, $\beta$, and $\gamma_1$ power variability and covariance between distant cortical sites during recovery.

FIGS. 3A and 3B are illustrations of trends in $\mu$, $\beta$, and $\gamma_1$ power variability and covariance between distant cortical sites during induction and recovery, respectively. All 95% confidence intervals were bootstrapped across subjects (n=7 for induction, n=6 for recovery). Average normalized $\mu$, $\beta$, and $\gamma_1$ power from an exemplar electrode demonstrating increased variance during induction that decreases on recovery. The median variance in power shows an increase with induction that decreases upon recovery. The mean intra-band power correlation between electrodes, that is, power in the $\mu$, $\beta$, and $\gamma_1$ bands shows increasing covariance during induction and a decrease during recovery. The median $\mu$, $\beta$, and $\gamma_1$ power covariance between electrodes shows an increase with induction that decreases upon recovery, following a similar pattern as the variance.

Band power covariance between cortical sites was analyzed for all frequency bands, revealing an increase in $\mu$, $\beta_{1-2}$, and $\gamma_1$ covariance during late induction, prior to the LOC. During recovery, covariance in these same bands was found to drop just subsequent to the discontinuation of propofol and to remain relatively unchanged to the ROC. The $\delta$ and $\gamma_4$ bands did not reflect these changes in covariance. This trend in $\mu/\beta_{1-2}/\gamma_1$ covariance was significant by bootstrapping and appears to have similar temporal behavior to the variance trends in this same frequency range.

The cortical networks defined by slow cortical potential (<0.1 Hz) covariance over the somatomotor cortex remained relatively unchanged throughout induction and recovery (see FIGS. 4A and 4B). Using an inferior motor cortex electrode as a seed, a region of statistically significant covariance (p>0.001) was identified in five epochs for both induction and recovery. These regions of covariance were found to remain relatively stable, with some fluctuation in the strength of the correlation. In the three subjects from whom ECoG signals were also acquired during burst suppression, these somatomotor covariance patterns appeared to be similarly maintained during this extreme depth of anesthesia (see FIGS. 5A, 5B, and 5C). This analysis was performed in four subjects with preferential electrode coverage of somatomotor cortex. Investigation of the SCP power revealed no significant changes during induction and recovery across subjects.

FIGS. 4A and 4B are illustrations of the correlation coefficient (p<0.001) of the slow cortical potential (<0.1 Hz) with an inferior motor cortex seed electrode in four patients with preferential somatomotor coverage during induction and recovery, respectively. The covariance structure is computed on the induction (FIG. 4A) and recovery (FIG. 4B) data in five consecutive epochs. Slight variations in these somatomotor covariance networks can be observed throughout induction and recovery, however their basic structure remains intact.

Figure 5A:
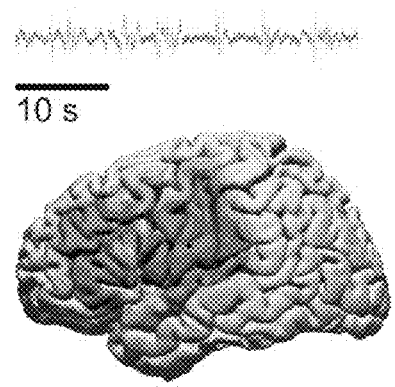
FIG. 5A is an illustration of the correlation coefficient of the slow cortical potential with an inferior motor cortex seed electrode in subject 2 during the period of burst suppression shown.
Figure 5B:
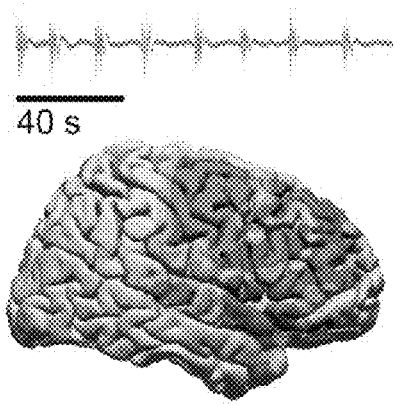
FIG. 5B is an illustration of the correlation coefficient of the slow cortical potential with an inferior motor cortex seed electrode in subject 5 during the period of burst suppression shown.
Figure 5C:
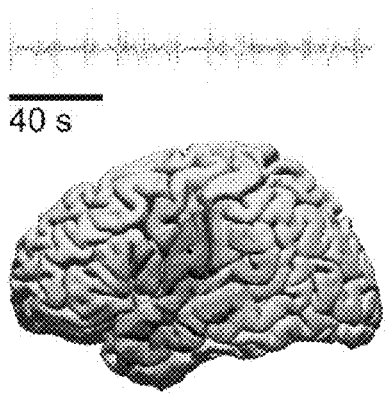
FIG. 5C is an illustration of the correlation coefficient of the slow cortical potential with an inferior motor cortex seed electrode in subject 6 during the period of burst suppression shown.

FIGS. 5A, 5B, and 5C are illustrations of the correlation coefficient of the slow cortical potential with an inferior motor cortex seed electrode in subject 2, subject 5, and subject 6, respectively, during the period of burst suppression shown. The relationship between signal phase and power was assessed by computing the correlation between the average trough-aligned, bandpass filtered signal and the similarly aligned average band power. An increased covariant relationship between the 1-4 Hz signal phase with the $\beta_2$-$\gamma_3$ signal power was seen with induction and decreased during recovery (see FIG. 6A). FIGS. 6B and 6C demonstrate this increased coupling of delta phase to gamma range power with data from a single exemplar electrode. A more finely resolved temporal progression of this phase-power coupling between delta and gamma range frequencies can be seen in FIGS. 7A and 7B. The phase of 4-12 Hz signal oscillations and the power in the $\gamma_{2-3}$ band were found to have an anti-correlated relationship, as previously described by Canolty et al, but did not appear to demonstrate noticeable changes with induction or recovery. Additionally, an anti-correlation between the phase of 1-4 Hz signal oscillations and the power in the θ and μ ranges was noted, but also did not appear to change across the four epochs of induction or recovery.

Figure 6A:
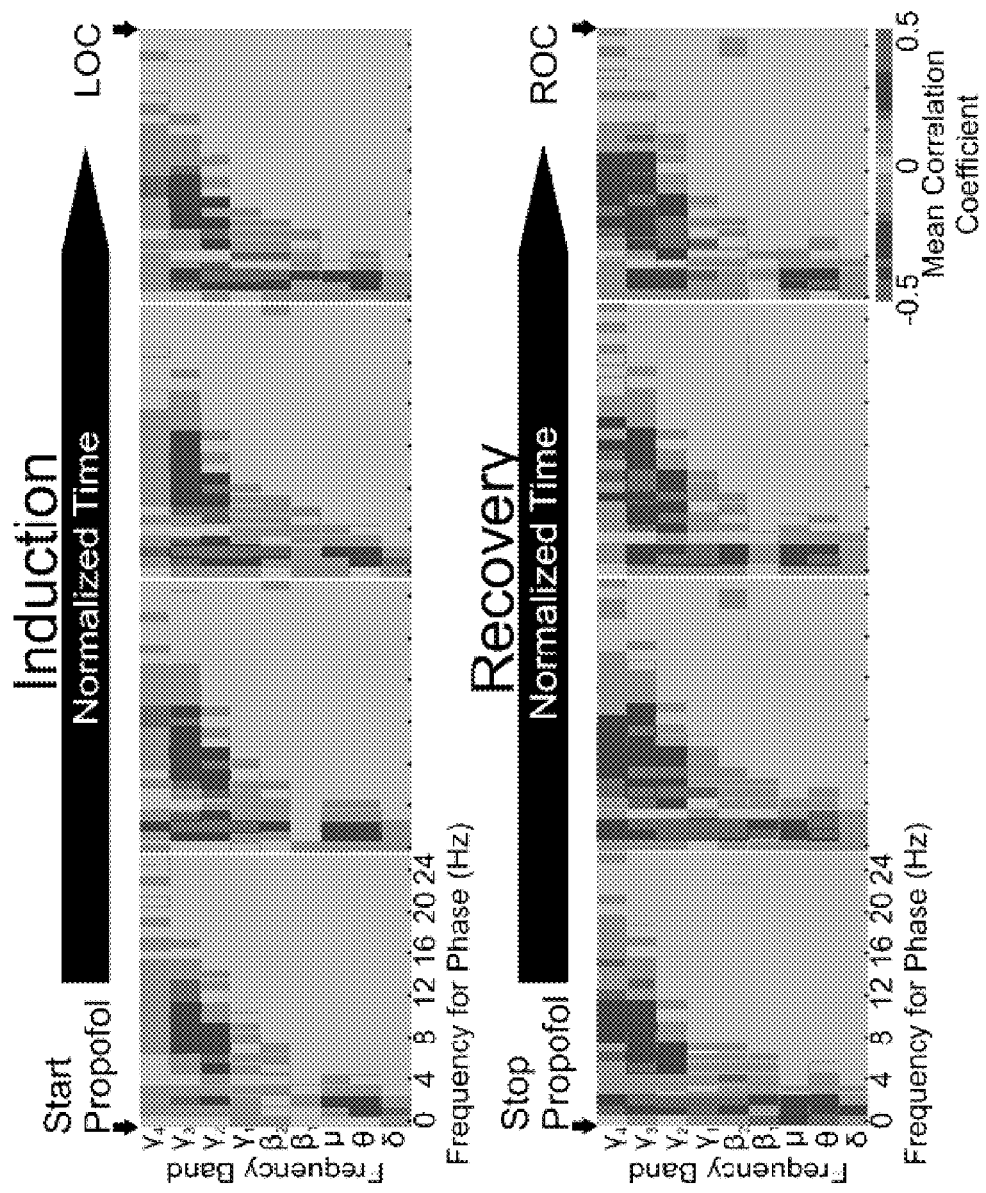
FIG. 6A is an illustration of phase-power correlations during induction and recovery.
Figure 6B:
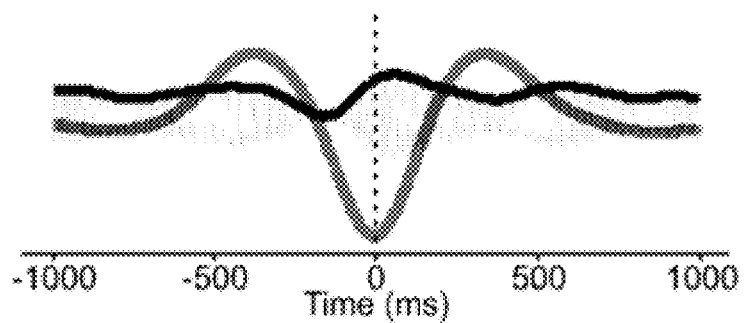
FIG. 6B is an illustration of the relationship between delta phase and high frequency power which emerges during early induction.
Figure 6C:
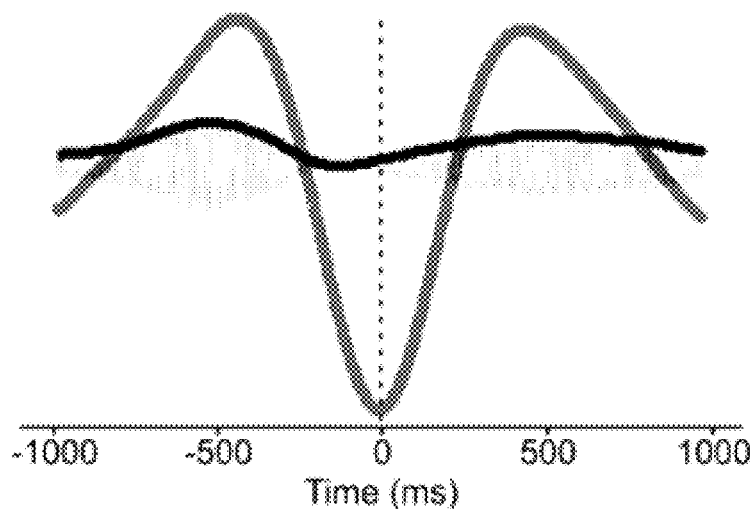
FIG. 6C is an illustration of the relationship between delta phase and high frequency power which emerges during late induction.

FIG. 6A is an illustration of phase-power correlations during induction and recovery. FIG. 6B is an illustration of the relationship between delta phase and high frequency power which emerges during early induction. FIG. 6C is an illustration of the relationship between delta phase and high frequency power which emerges during late induction. Referring to FIG. 6A, the mean correlation coefficient (p>0.001 for contributing coefficients) between the average trough-aligned bandpass-filtered component of the ECoG signal and the power in the nine frequency bands. A correlation between the phase of 1-4 Hz and power of the $\beta_2$-$\gamma_3$ bands strengthens during induction and diminishes during recovery. Anti-correlation between 4-12 Hz phase and $\gamma_{2-3}$ power and between 1-4 Hz phase and θ-μ power can also be seen. Referring to FIGS. 6B and 6C, data from an exemplar electrode illustrates the relationship between delta phase and high frequency power which emerges during induction. The average trough-aligned 1-4 Hz filtered component (blue) and the average $\gamma_2$ power (black) from the first and fourth time epochs during induction.

Figure 7A:
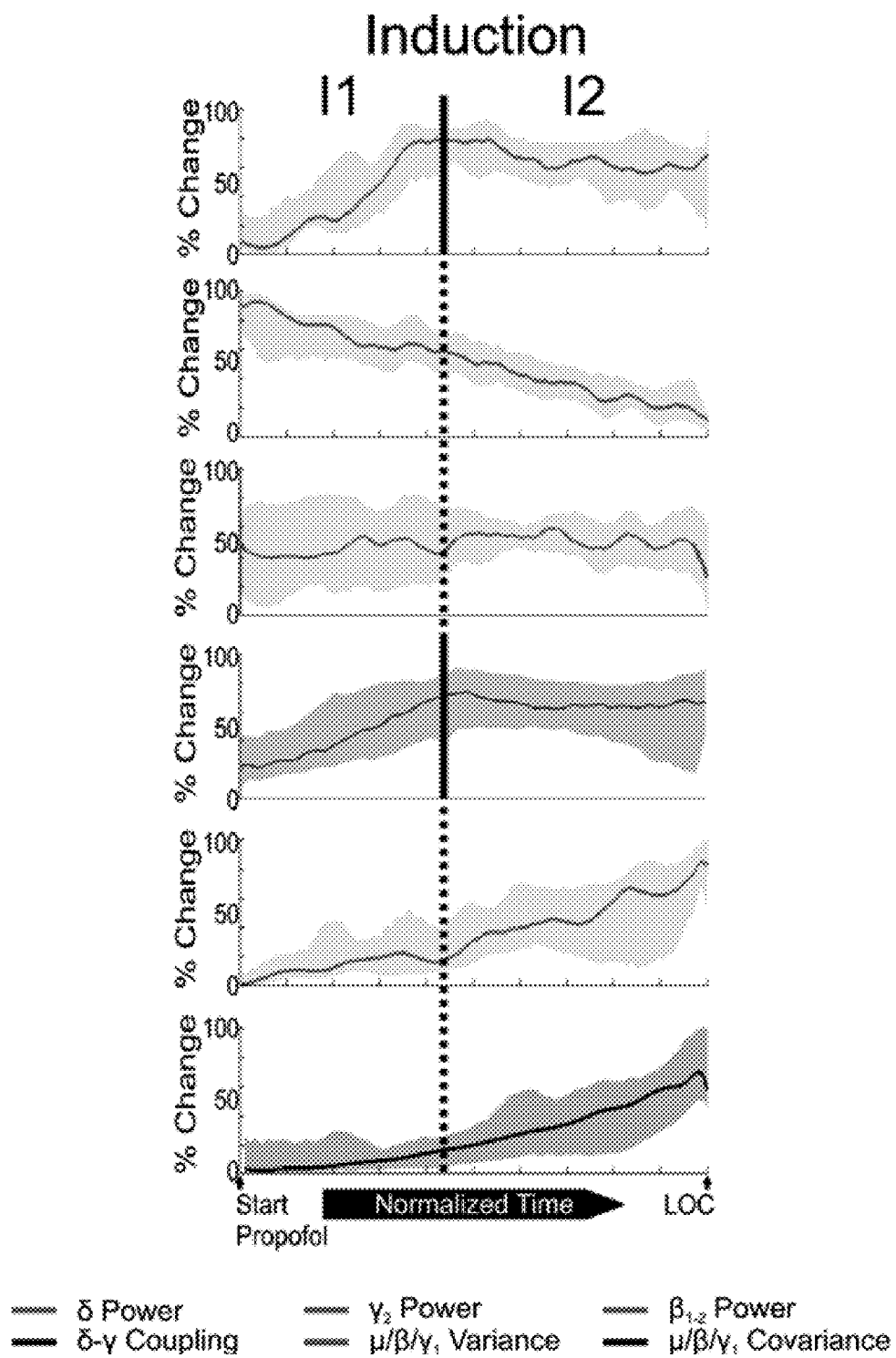
FIG. 7A is an illustration of phases of change in spectral power, variance, covariance, and phase-power coupling during induction.
Figure 7B:
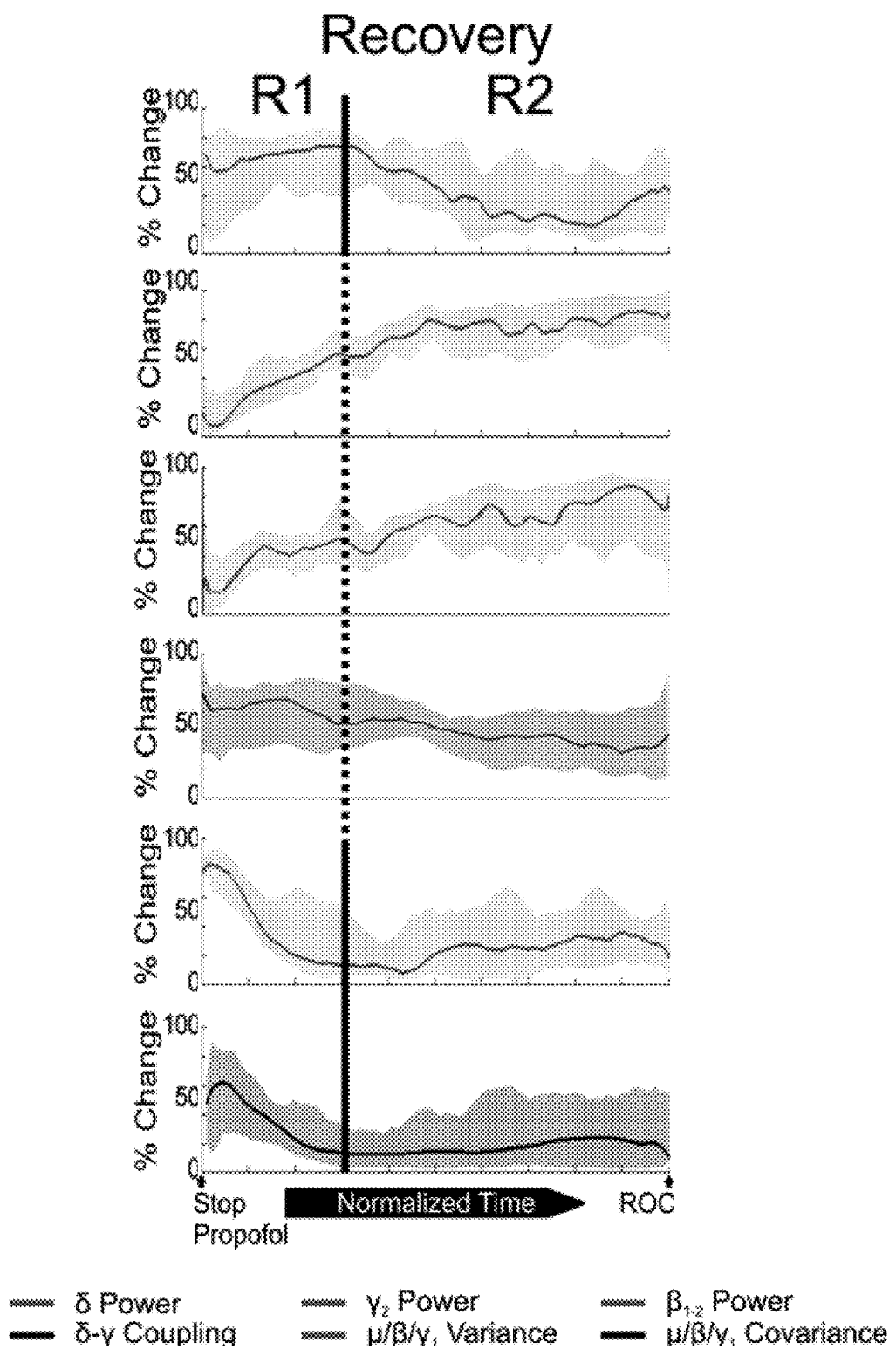
FIG. 7B is an illustration of phases of change in spectral power, variance, covariance, and phase-power coupling during recovery.

The temporal relationships of the trends in electrocortical band power, variance, covariance, and phase-power coupling during induction and recovery are summarized in FIGS. 7A and 7B. Piecewise linear regression modeling identified breakpoints within some trends, identifying separable physiologic phases for both induction and recovery from anesthesia ($R^2$=0.135 to 0.402). Power changes in the δ and γ bands, and coupling between these bands, are the first to occur during induction (see Induction Phase 1, I1), with δ rising and leveling off while γ power shows a continual decrease all the way to LOC. Following the peaking of δ power and δ-γ coupling, there is increased μ-$\beta_{1-2}$-$\gamma_1$ variability in power leading up to LOC (Induction Phase 2, I2). This increased waxing and waning of μ-β-low γ oscillations is coherent across the cortex, as indicated by the simultaneous rise in μ-β-$\gamma_1$ band power covariance between cortical sites. $\beta_{1-2}$ power exhibits no overall increase or decrease throughout induction.

During recovery, these changes reverse themselves in a similar stepwise yet asymmetric fashion. Following discontinuation of propofol, the effects in the μ-β-$\gamma_1$ band reverse themselves; γ and $\beta_{1-2}$ power also begin to increase rapidly (Recovery Phase 1, R1). After the μ-β-$\gamma_1$ band variance and covariance has reached relatively stable values, the δ power and δ-γ coupling decreases and levels off. Finally, the rate of γ and $\beta_{1-2}$ power increases appears to slow (Recovery Phase 2, R2).

FIGS. 7A and 7B are illustrations of phases of change in spectral power, variance, covariance, and phase-power coupling during induction and recovery, respectively. Solid vertical lines demarcate mean knot sites, where segments were found to be separable with adaptive piecewise regression. These demarcations were used to separate the different phases of inductions and recovery. During induction phase 1 (I1), δ power (blue) and δ phase-$\gamma_2$ power coupling (purple) increase. Throughout induction, $\gamma_{1-4}$ power (red) declines. A rise in μ, $\beta_{1-2}$, and $\gamma_1$ variance (green) and covariance (black) occurs during induction phase 2 (I2). During recovery phase 1 (R1), μ, $\beta_{1-2}$, and $\gamma_1$ variance and covariance decrease, as γ and $\beta_{1-2}$ (cyan) power begin to rise. During recovery phase 2 (R2), δ power and δ-$\gamma_2$ coupling decrease, while γ and $\beta_{1-2}$ power continue to rise. This $\beta_{1-2}$ band power change is asymmetric between induction and recovery. (A) δ power. (B) $\gamma_2$ power. (C) $\beta_{1-2}$ power. (D) δ phase-$\gamma_2$ power coupling. (E) μ, $\beta_{1-2}$, and $\gamma_1$ power variability. (F) μ, β, and $\gamma_1$ power covariance. All trends reflect the smoothed median and bootstrapped 95% confidence interval.

Figure 8:
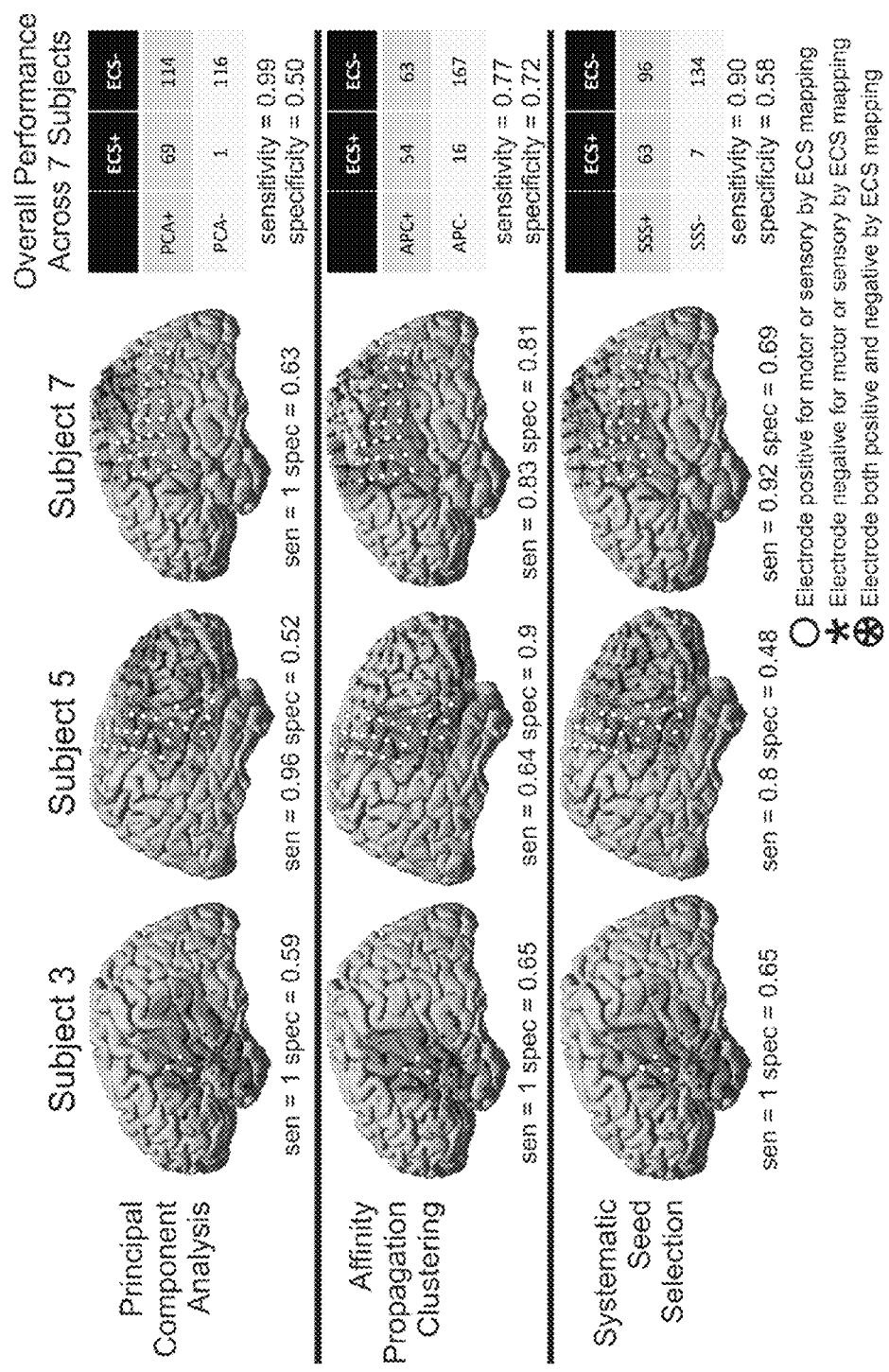
FIG. 8 is an illustration of sensitivity and specificity of three approaches to using SCP covariance for mapping somatomotor cortex in unconscious subjects.

Finally, analysis of the sensitivity and specificity of three approaches to using SCP covariance of baseline ECoG data from fully anesthetized patient to identify functional somatomotor cortex is shown in FIG. 8. Data from three exemplar subjects is shown in addition to the summary performance data across all seven subjects. Principal component analysis was 99% sensitive and 50% specific, affinity propagation clustering was 77% sensitive and 72% specific, and systematic seed selection was 90% sensitive and 58% specific.

FIG. 8 is an illustration of sensitivity and specificity of three approaches to using SCP covariance for mapping somatomotor cortex in unconscious subjects. Exemplar data is shown from three of the seven subjects analyzed. The PCA based method had the highest sensitivity (99%), while the method of affinity propagation clustering achieved the highest specificity (72%).

To establish a proof of concept, methods described herein were applied in a post hoc fashion to compare against the current gold standard of electrocortical stimulation of an awake patient. The SCP covariance structures below are based on data recorded from an unresponsive anesthetized surgical patient. The seeds were chosen based on SIGFREID activations seen in response to hearing speech from the surgeon. The patient was asked to imagine moving their tongue. Seed 22 identified 19 and 23 which were positive for speech arrest with ECS, as well as what appeared to be auditory cortex. Seed 12 identified motor cortex, and electrode 21 was positive for speech arrest with stimulation.

Figures 9A, 9B:
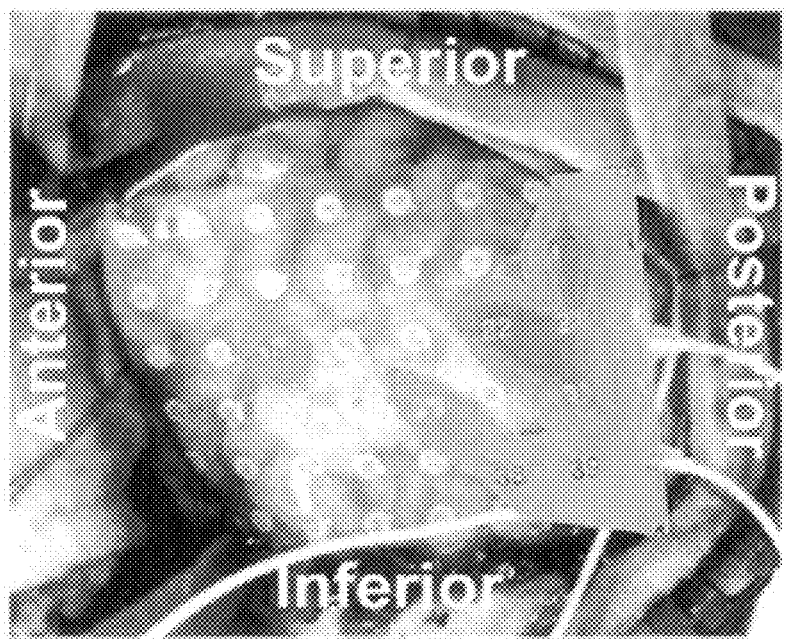
FIG. 9A is an illustration of localization of the speech cortex in a grid format.
FIG. 9B is an illustration of localization of the speech cortex with an overlay of the grid from FIG. 9A.

FIG. 9A is an illustration of localization of the speech cortex in a grid format. FIG. 9B is an illustration of localization of the speech cortex with an overlay of the grid from FIG. 9A.

Figure 10A:
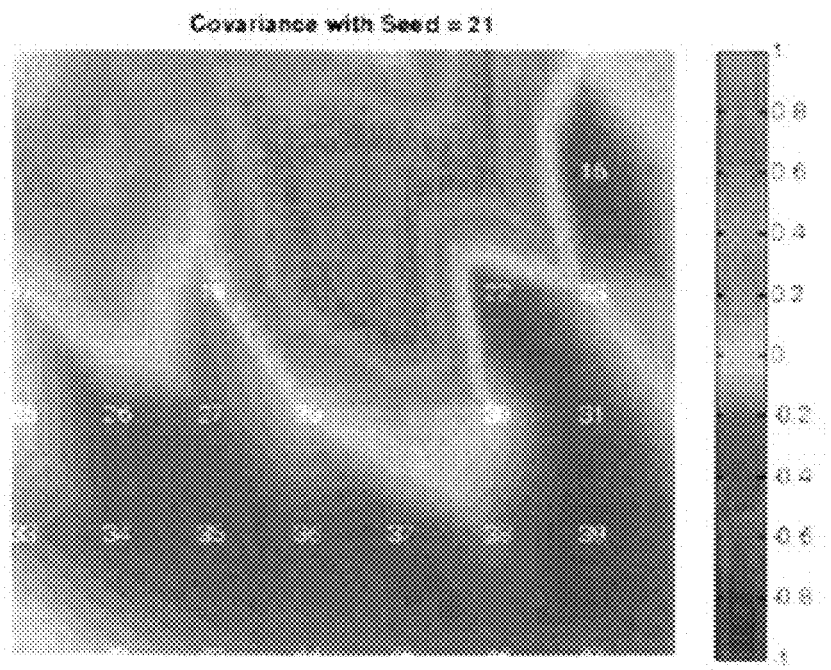
FIG. 10A is an illustration of localization of the motor cortex in a grid format.
Figure 10B:
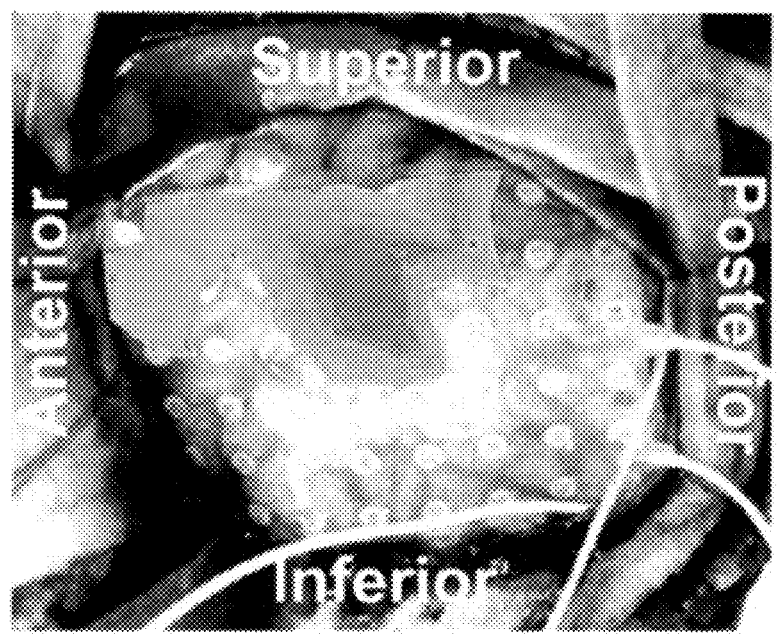
FIG. 10B is an illustration of localization of the motor cortex with an overlay of the grid from FIG. 10A.

FIG. 10A is an illustration of localization of the motor cortex in a grid format. FIG. 10B is an illustration of localization of the motor cortex with an overlay of the grid from FIG. 10A.

Unlike known tools, embodiments provided herein facilitate identification of language cortex in unconscious patients who are not candidates for awake craniotomy, and would serve as an adjunct intraoperative mapping tool for patients who are candidates for awake craniotomy. Moreover, such embodiments facilitate eliminating the need for awake mapping in neurosurgical patient all together.

Methods—Anesthesia

Initial Craniotomy for Grid Placement: Recovery of Consciousness (ROC) Data Collection Upon arrival in the operating room, the patients were monitored according to the American Society of Anesthesiologists' (ASA) guidelines. In addition, a bispectral index (BIS) monitor (Aspect Medical Systems Inc. Norwood, Mass.) was placed on the forehead on the side opposite to the surgical field. After pre-oxygenation by mask, the induction was carried out with a combination of propofol and fentanyl; intravenous boluses were titrated to the loss of eyelid reflexes. Vecuronium was administered for pharmacologic muscle relaxation to facilitate tracheal intubation. Maintenance of anesthesia consisted of a propofol infusion at 100-200 mcg/kg/min, fentanyl infusion at 1-5 mcg/kg/hr and vecuronium as needed for muscle relaxation. Throughout the procedure, the end tidal carbon dioxide ($EtCO_2$) was maintained between 25 and 35 mmHg with mechanical ventilation. The fentanyl infusion was discontinued approximately 45 minutes prior to the anticipated awakening period. After closure and dressing of the surgical wound, the residual pharmacologic relaxation was antagonized and the propofol infusion was discontinued. Simultaneously, the ECoG electrodes were connected to the recorders and the data collection started while the patients were allowed to awaken in a quiet environment. The BIS value was recorded manually every 30 seconds. As soon as the patients started to show signs of rousing, they were intermittently asked to follow a verbal command, such as "squeeze my hand" or "wiggle your toes," approximately every 60 seconds until they followed commands. This time point was designated as return of responsiveness (ROC). When patients were awake, the tracheal tube was removed, the ECoG electrodes were disconnected, and the patients were transferred to the neurosurgical intensive care unit.

Monitoring for Localization of Epileptogenic Foci

First in the neurosurgical intensive care unit and subsequently in the epilepsy monitoring unit, the patients were continuously monitored with clinical video and ECoG recording equipment for a period of approximately one week. During this time anticonvulsant medications were discontinued in order to promote seizure activity and facilitate foci mapping. Pain was controlled with morphine and oxycodone/acetaminophen as needed, but no sedatives or other hypnotics were administered during the entire diagnostic phase in order to avoid seizure suppression.

Induction of Anesthesia for Craniotomy for Grid Removal with Foci Excision: Loss of Consciousness (LOC) Data Collection Once the diagnostic phase of the epilepsy treatment had been completed, the patients were returned to the operating room for a second craniotomy for the ECoG grid removal and foci resection. Anesthesia monitoring was identical to the initial procedure. Patients received no sedative or analgesic premedication. Prior to induction of anesthesia, patients received high concentration oxygen by face mask while the ECoG electrodes were connected to the recorders and data collection commenced. The propofol infusion was then started. Propofol requirements to achieve burst suppression on ECoG in humans have been shown to be extremely variable among patients. Because of the high degree of inter-patient variability in responsiveness to propofol (14), we elected to proceed with a propofol infusion given in a controlled, continuous and progressive fashion to facilitate a prolonged transition between the awake pre-induction state of responsiveness to verbal commands, and the endpoint of unresponsiveness to verbal commands and loss of the eyelid reflex. This was achieved by incrementally increasing the propofol infusion rate by 50-100 mcg/kg/min every 3-5 min based on clinical examination for spontaneous eye opening, movements and reaction to environmental stimuli. BIS data were manually recorded every 30 seconds. Once the patients began to show signs of increased levels of sedation, the response to verbal commands was assessed approximately every 60 seconds until loss of responsiveness (LOC) to command was observed, at which point the ECoG recording was discontinued. During the entire induction period, the $EtCO_2$ and oxygen saturation were maintained between 30 to 35 mmHg, and 98 to 100% respectively, if needed by supporting ventilation manually. Following LOC, the usual anesthetic and surgical management of the patients ensued.

Figure 11:
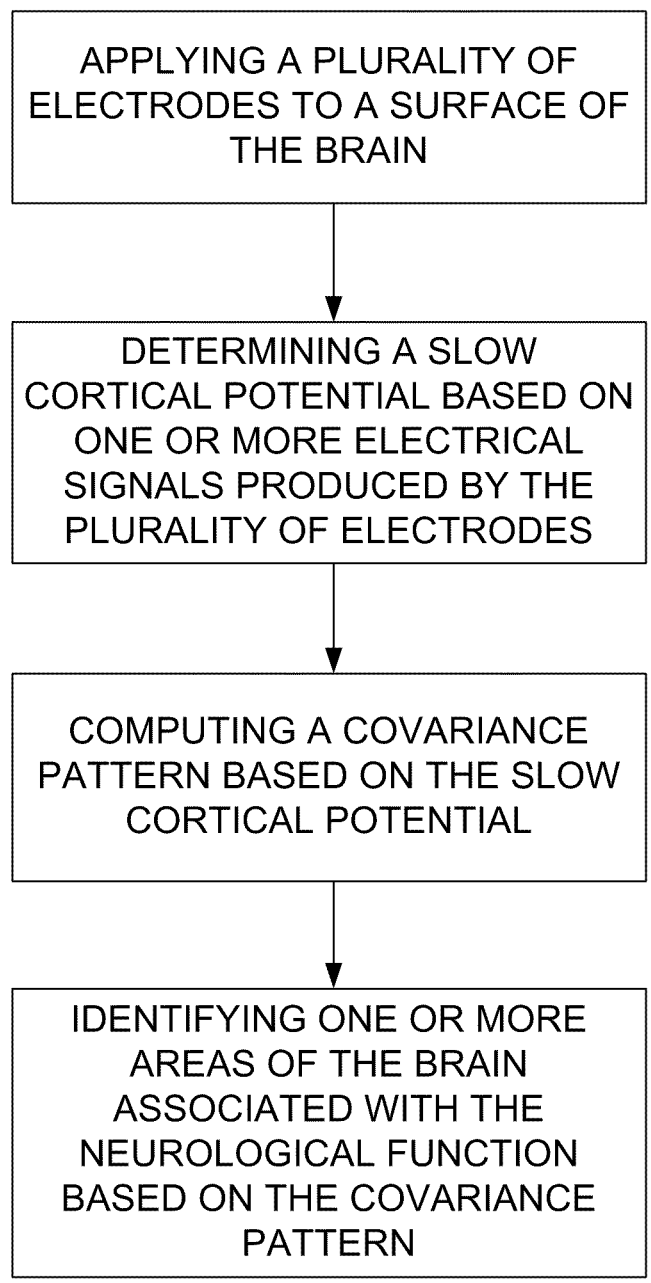
FIG. 11 is a flow chart of a first method for identifying a functional area of a brain, wherein the functional area is associated with a neurological function.

FIG. 11 is a flow chart of a first method for identifying a functional area of a brain, wherein the functional area is associated with a neurological function.

Figure 12:
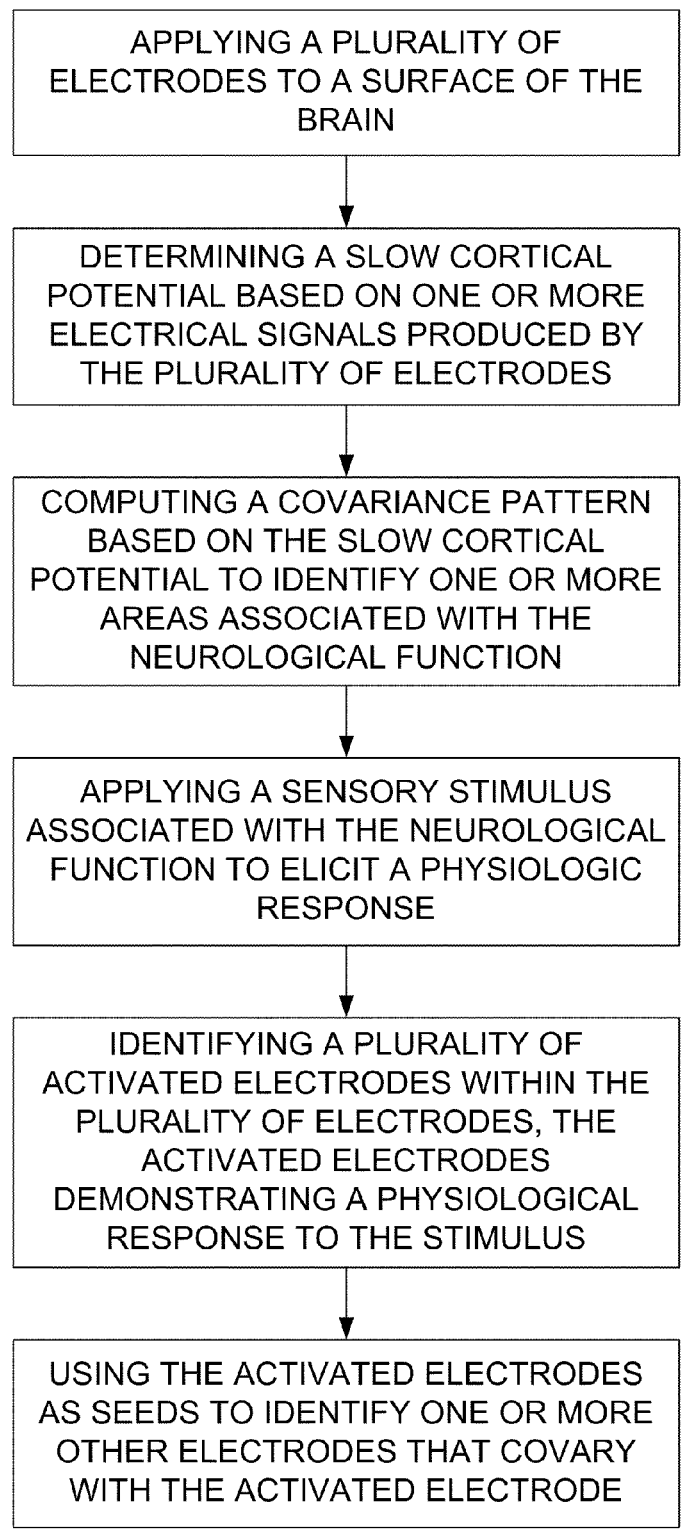
FIG. 12 is a flow chart of a second method for identifying a functional area of a brain, wherein the functional area is associated with a neurological function.

FIG. 12 is a flow chart of a second method for identifying a functional area of a brain, wherein the functional area is associated with a neurological function.

Table S1 includes demographic and clinical information for the eight subjects. Induction duration was measured between the start of the propofol infusion and the LOC. Recovery duration was measured from the discontinuation of the propofol maintenance infusion to the ROC. These estimates are CP=Complex Partial; ATL=Anterior Temporal Lobe; PFL=Posterior Frontal Lobe; MPL=Medial Parietal Lobe.

TABLE S1

| Subject | Sex | Age | Seizure Type | Seizure Foci | Induction Duration (min) | Recovery Duration (min) |
| --- | --- | --- | --- | --- | --- | --- |
| 1 | F | 44 | CP | ATL | 15 | 21 |
| 2 | F | 49 | CP | ATL | 12 | 43 |
| 3 | M | 36 | CP | ATL | 14 | 36 |
| 4 | M | 52 | CP | PFL | 16 | 24 |
| 5 | F | 28 | CP | PFL | 14 | 16 |
| 6 | F | 48 | CP | ATL | — | 14 |
| 7 | M | 27 | CP | MPL | 23 | — |
| 8 | M | 21 | CP | MPL | 18 | — |

Exemplary Operating Environment

Collection and analysis of ECoG data such as described herein is typically performed by a computer or computing device. A computer or computing device includes one or more processors or processing units, system memory, and some form of computer readable media. By way of example and not limitation, computer readable media comprise computer storage media and communication media. Computer storage media include volatile and nonvolatile, removable and non-removable media implemented in any method or technology for storage of information such as computer readable instructions, data structures, program modules or other data. Communication media typically embody computer readable instructions, data structures, program modules, or other data in a modulated data signal such as a carrier wave or other transport mechanism and include any information delivery media. Combinations of any of the above are also included within the scope of computer readable media.

Although described in connection with an exemplary computing system environment, embodiments of the invention are operational with numerous other general purpose or special purpose computing system environments or configurations. The computing system environment is not intended to suggest any limitation as to the scope of use or functionality of any aspect of the invention.

When introducing elements of aspects of the invention or embodiments thereof, the articles "a," "an," "the," and "said" are intended to mean that there are one or more of the elements. The terms "comprising," including," and "having" are intended to be inclusive and mean that there may be additional elements other than the listed elements.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for identifying a functional area of a brain in an unconscious neurosurgical patient, the functional area associated with a neurological function, the method comprising:
   applying a plurality of electrodes to a surface of the brain;
   assigning a level of consciousness to the neurosurgical patient;
   determining a slow cortical potential based on one or more electrical signals produced by the plurality of electrodes;
   computing a covariance pattern based on the slow cortical potential; and
   identifying one or more areas of the brain associated with the neurological function based on the covariance pattern.

2. The method of claim 1, further comprising applying a sensory stimulus associated with the neurological function to elicit a physiological response.

3. The method of claim 1, wherein identifying one or more areas of the brain associated with the neurological function comprises identifying one or more areas of the brain associated with one or more of the following:
   speech;
   motor function;
   vision;
   attention; and
   hearing.

4. The method of claim 1, wherein the neurological function is a part of normal human cognitive operation.

5. The method of claim 1, wherein the neurological function is a part of abnormal human cognitive operation.

6. The method of claim 5, wherein identifying one or more areas of the brain associated with the neurological function comprises identifying one or more areas of the brain associated with seizures.

7. The method of claim 5, wherein identifying one or more areas of the brain associated with the neurological function comprises identifying one or more areas of the brain associated with schizophrenia.

8. The method of claim 5, wherein identifying one or more areas of the brain associated with the neurological function comprises identifying one or more areas of the brain associated with mood disorders.

9. The method of claim 5, wherein identifying one or more areas of the brain associated with the neurological function comprises identifying one or more areas of the brain associated with autism.

10. The method of claim 5, wherein identifying one or more areas of the brain associated with the neurological function comprises identifying one or more areas of the brain associated with neurodegenerative disorders.

11. The method of claim 5, wherein identifying one or more areas of the brain associated with the neurological function comprises identifying one or more areas of the brain associated with attentional disorders.

12. The method of claim 5, wherein identifying one or more areas of the brain associated with the neurological function comprises identifying one or more areas of the brain associated with stroke.

13. A method for identifying a functional area of a brain in an unconscious neurosurgical patient, the functional area associated with a neurological function, the method comprising:
   applying a plurality of electrodes to a surface of the brain;
   assigning a level of consciousness to the neurosurgical patient;
   determining a slow cortical potential based on one or more electrical signals produced by the plurality of electrodes;
   computing a covariance pattern based on the slow cortical potential to identify one or more areas associated with the neurological function;
   applying a sensory stimulus associated with the neurological function to elicit a physiologic response;
   identifying a plurality of activated electrodes within the plurality of electrodes, the activated electrodes demonstrating a physiological response to the stimulus; and
   using the activated electrodes as seeds to identify one or more other electrodes that covary with the activated electrodes.

14. The method of claim 13, wherein applying a sensory stimulus associated with the neurological function to elicit a physiologic response comprises one or more of the following:
   applying an auditory stimulus;
   applying a painful or proprioceptive stimulus;
   applying a visual stimulus;
   applying an olfactory stimulus;
   applying a taste stimulus; and
   applying a motor stimulus.

15. The method of claim 13, further comprising comparing an anatomic distribution of a plurality of covariance patterns to other anatomic data.

16. The method of claim 15, wherein comparing an anatomic distribution of a plurality of covariance patterns to other anatomic data comprises comparing the anatomic distribution to magnetic resonance imaging data.

17. The method of claim 15, wherein comparing an anatomic distribution of a plurality of covariance patterns to other anatomic data comprises comparing the anatomic distribution to functional magnetic resonance imaging data.

18. The method of claim 15, wherein comparing an anatomic distribution of a plurality of covariance patterns to other anatomic data comprises comparing the anatomic distribution to computed tomography data.

19. The method of claim 15, wherein comparing an anatomic distribution of a plurality of covariance patterns to other anatomic data comprises comparing the anatomic distribution to positron emission tomography data.

20. The method of claim 15, wherein comparing an anatomic distribution of a plurality of covariance patterns to other anatomic data comprises comparing the anatomic distribution to imaging data representing resting state functional connectivity.

* * * * *